Figure 3:

United States Patent [19]

Ståhl et al.

[11] Patent Number: 5,958,736

[45] Date of Patent: Sep. 28, 1999

[54] RECOMBINANT DNA CODING FOR SIGNAL PEPTIDE, SELECTIVE INTERACTING POLYPEPTIDE AND MEMBRANE ANCHORING SEQUENCE

[75] Inventors: Stefan Ståhl, Görvik; Per-Åke Nygren, Pilotgatan; Marianne Hansson, Blåsutyägen; Mathias Uhlén, Kvarnbogatan, all of Sweden; Thien Ngoc Nguyen, St. Julien, France

[73] Assignee: Pierre Fabre Medicament, Boulogne, France

[21] Appl. No.: 08/629,039

[22] Filed: Apr. 8, 1996

Related U.S. Application Data

[63] Continuation of application No. 08/140,138, Nov. 3, 1993, abandoned.

[30] Foreign Application Priority Data

May 13, 1991 [SE] Sweden .................................. 9101433

[51] Int. Cl.⁶ .................................................. C12N 15/00
[52] U.S. Cl. ........................ 435/69.7; 435/69.3; 435/69.1; 435/69.8; 435/7.1; 435/172.1; 435/252.3; 435/253.4; 435/882; 435/883; 424/192.1; 536/23.5
[58] Field of Search ................................ 435/69.1, 252.3, 435/320.1, 69.3, 69.7, 7.1, 882, 883, 69.8, 71.1, 172.1, 253.4; 424/192.1; 536/23.5

[56] References Cited

U.S. PATENT DOCUMENTS 5,200,327  4/1993  Garvin et al. ........................... 435/69.5

FOREIGN PATENT DOCUMENTS

WO 88/06630  9/1988  WIPO .

OTHER PUBLICATIONS

Uhlen et al., Methods in Enzymology 185: 129–143, 1990.
Uhlen et al., Journal of Bacteriology 159(2):713–719, Aug. 1984.
Smith, Science 228: 1315–1317, Jun. 1985.

*Primary Examiner*—John Ulm
*Assistant Examiner*—Eliane Lazar-Wesley
*Attorney, Agent, or Firm*—Burns, Doane, Swecker & Mathis, L.L.P.

[57] ABSTRACT

Tripartite recombinant DNA encoding fusion proteins which comprise three sequences, i.e., a signal peptide which is operable in a Gram positive bacterium, an immunogenic polypeptide linked thereto which is not normally expressed in a Gram positive bacterium, and a cell wall spanning and a membrane anchoring sequence, as well as their use in Gram positive bacteria to express the resultant fusion protein on their surface are described. The preferred cell wall spanning and anchoring polypeptides include Staphylococcus protein A and Streptococcus protein G.

41 Claims, 8 Drawing Sheets

FIG. IA
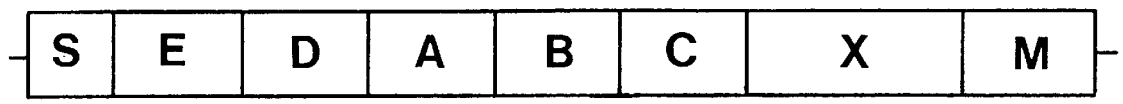
FIG. IB
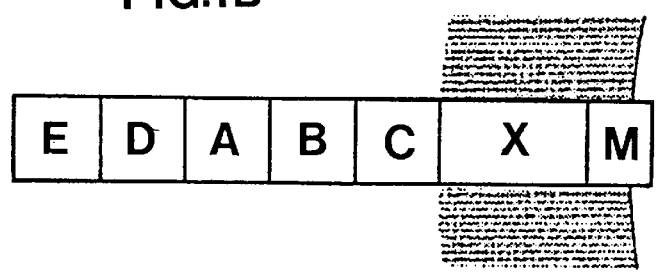
FIG. 7
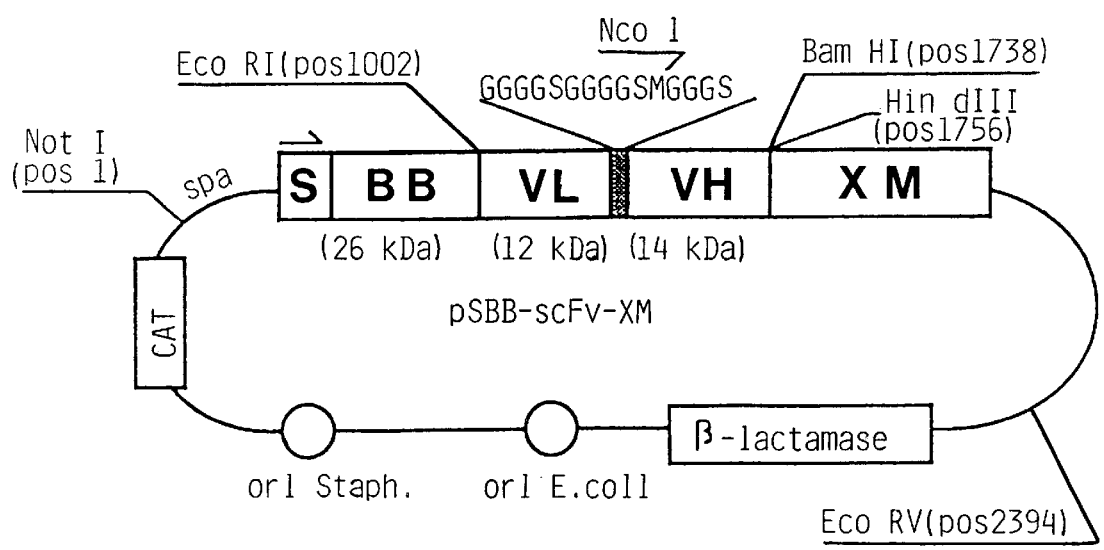

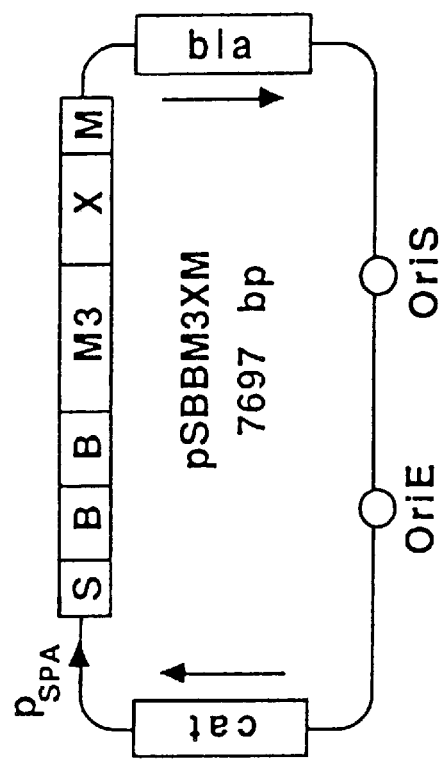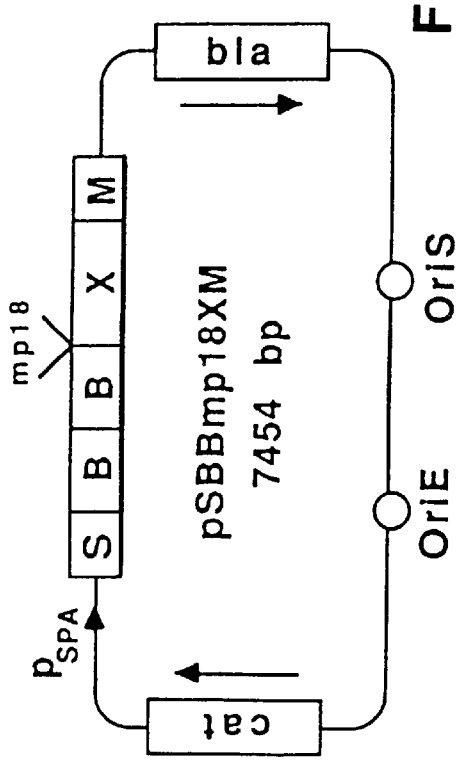
FIG.2A
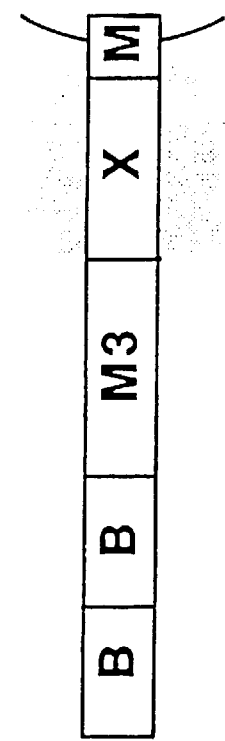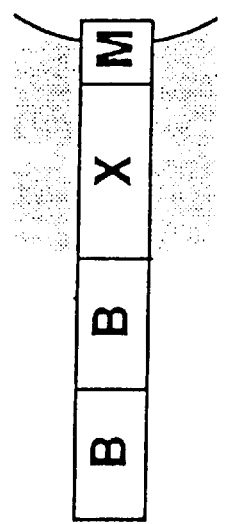
FIG.2B

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 29 base pairs
      (B) TYPE: nucleic acid
      (C) STRANDEDNESS: single (D) TOPOLOGY: linear (ii) MOLECULE TYPE: DNA (genomic)

(xi) SEQUENCE DESCRIPTION: SEQ ID NO:1:

CCGAATTCGC AGGTCCAACT GAAGGAGTC                                              29

(2) INFORMATION FOR SEQ ID NO:2:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CGAAGCTTTT AGGATCCTGA GGAGACTGTG AGAGTGG                                     37

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCGAATTCGG ACATCCAGAT GACTCAGTC                                              29

(2) INFORMATION FOR SEQ ID NO:4:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGAAGCTTTT AGGATCCTTT GATTTCCAGC TTGGTGCC                                    38

(2) INFORMATION FOR SEQ ID NO:5:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TGGACCCACC ACCGCCCGAG CCACCGCCAC CTTTGATTTC CAGCTTGGTG CC                    52

(2) INFORMATION FOR SEQ ID NO:6:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GGGCGGTGGT GGGTCCATGG GCGGCGGATC TCAGGTCCAA CTGAAGGAGT C          51
```

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
TTGGATCCTG CAGCAATTT                                              19
```

(2) INFORMATION FOR SEQ ID NO:8:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CCGAATTCAA GCTTCGCTCA AGCACCAAAA GAGGAAGACA ATAAC                 45
```

(2) INFORMATION FOR SEQ ID NO:9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
ATGTATCTAT CTGCTCTAAC AACCCGACTT GTTGGGCTAT CTCCAAAA              48
```

(2) INFORMATION FOR SEQ ID NO:10:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
ACATTTTTGG AGATAGCCCA ACAAGTCGGG TTGTTAGAGC AGATAGAT              48
```

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GGGGSGGGGS MGGGS                                                  15
```

RECOMBINANT DNA CODING FOR SIGNAL PEPTIDE, SELECTIVE INTERACTING POLYPEPTIDE AND MEMBRANE ANCHORING SEQUENCE

This application is a continuation of application Ser. No. 08/140,138, filed Nov. 3, 1993, now abandoned.

The present invention relates to a recombinant DNA sequence substantially comprising three different DNA fragments, and to expression vectors or plasmids containing such sequence, as well as Gram positive bacterial cells harbouring such DNA sequence or being transformed by a vector or plasmid as indicated. The invention furthermore involves a process for selective isolation or identification of Gram positive bacterial cells.

The present invention involves new useful techniques based on an entirely new concept involving utilization of surface receptor structures found on bacterial cells. These new techniques find many interesting applications, the two major aspects of the invention residing in curative or preventive immunology on the one hand and practical processes for selective isolation or identification of Gram positive bacterial cells on the other hand.

In modern vaccinology there is a great interest in the development of live delivery systems for recombinant immunogens, as live organisms often show enhanced immunogenicity over killed or subunit vaccine preparations. A number of live recombinant attenuated viruses have been tried as carriers of foreign epitopes. These include vaccinia virus (Moss et al., Nature 311, 67–69 (1984)), adenovirus (Ballay et al., EMBO J. 4, 3861–3865 (1985)), poliovirus (Evans et al., Nature 339, 385–388 (1989)) and herpesvirus (Shih et al., Proc. Natl. Acad. Sci. USA 81, 5867–5870 (1984)). Also bacterial systems, using live recombinant bacteria, such as Salmonella (Hosieth and Stocker, Nature 291, 238–239 (1981)), mycobacteria (Jacobs et al., Nature 327, 532–535 (1987)) and *E. coli* (O'Callaghan et al., Res. Microbiol. 141, 963–969 (1990)), have been developed where the whole bacterium is used as a carrier of the recombinant immunogen.

Furthermore, modern recombinant DNA techniques have made it possible to isolate and clone antibody genes directly from immunized animals or from in vitro immunized lymphocytes (Huse et al., Science, 1989, 246, 1275–1280) (Borrebaeck et al., Proc.Natl.Acad.Sci. USA 1988, 85, 3995–3999). Genetic libraries of the antibody repertoire can be established in bacterial vector systems, allowing easy in vitro manipulation of the isolated immunoglobulin genes.

By "random" combination of genes encoding the variable regions derived from heavy (VH) and light (VL) chains, and the subsequent expression in a bacterial host, new formations of VH/VL pairs are obtained that can be screened for binding characteristics. (Huse et al., Science, 1989, 246, 1275–1280). However, the large number of clones generated using this strategy calls for efficient screening methods to enable isolation of relevant clones in a practical manner. Recently, a strategy has been described employing bacterial phages as carriers of surface exposed immunoglobulin fragments, allowing selection of single phage particles bearing combinations of VH/VL domains capable of binding a desired antigen (McCafferty et al., 1990, Nature, 348, 552–554).

The importance of new techniques for the clone specific isolation of vehicles carrying unique surface exposed structures also relate to fields such as hormone-hormone receptor recognition (Bass et al., Proteins: Structure, Function and Genetics, 8, 309–314 (1990)) and enzymesubstrate compatibility (Carter et al., Proteins: Structure, Function and Genetics, 6, 240–248 (1989)).

However, structural constraints for the incorporation of immunoglobulin segments into the phage coat protein employed can result in negative biological selection and subsequent loss of the theoretical repertoire of VH/VL combinations. Moreover, the small number of immunoglobulin molecules exposed on each phage particle, from 1 to about 5 molecules, can result in insurmountable problems with regard to the recovery of combinations with moderate binding capabilities due to the low overall affinity of the phage particle.

Also systems for displaying heterologous proteins on the surface of *Escherichia coli* have been described, such as fusions of antigenic peptides to the flagellor filament (Kuwajima et al., 1988, Bio/Technology, 6, 1080–1083) or the outer membrane protein Lam B (O'Callaghan et al., 1990, Res.Microbiol. 141, 963–969). Here, again, there are structural constraints that make such concept less useful in practical applications.

The present invention has for its main object to provide new techniques based on the concept of using recombinant surface receptor structures for a wide spectrum of practical applications.

Another object of the invention is to use Gram positive bacteria as carriers for the presentation of immunogenes, whereby the immunogenic response is greatly improved and the use of conventional adjuvants less critical or even superfluous.

Yet another object of the invention is to provide techniques. enabling identification and/or isolation of Gram positive bacterial cells from a heterologous population of such cells carrying different recombinant surface receptor structures.

Further objects of the invention are to provide recombinant DNA sequences, expression vectors or plasmids containing such sequences and Gram positive bacterial cells harbouring such sequences or being transformed by such vector or plasmid.

For these and other purposes that will be evident from the following description the present invention provides a recombinant DNA sequence comprising a first DNA fragment coding for a first amino acid sequence operating as a signal peptide operable in a Gram positive host, operatively linked to a second DNA fragment coding for a second amino acid sequence not naturally found on the surface of Gram positive bacteria and capable of selective interaction, said second DNA fragment being operatively linked to a third DNA fragment coding for a third amino acid sequence operable in a Gram positive host as a cell wall spanning and membrane anchoring sequence.

In such recombinant DNA sequence said second amino acid sequence may be capable of antigenic action or may be constituted by an antibody (immunoglobulin) or an active fragment thereof.

In accordance with a preferred embodiment of the invention the recombinant DNA sequence is such wherein said third DNA fragment codes for the cell wall spanning and membrane anchoring region of staphylococcal protein A or streptococcal protein G.

In accordance with a preferred aspect of the invention said first DNA fragment originates from a Gram positive bacterial cell, such as a DNA fragment coding for the signal peptide of staphylococcal protein A.

Said third DNA fragment preferably codes for the cell wall spanning and membrane anchoring region of staphylococcal protein A.

With regard to the immunological aspect of the invention it is preferred that said second DNA fragment codes for an amino acid sequence capable of eliciting an immunogenic response that will be useful for vaccination purposes or for the production of antibodies.

The invention also involves the provision of an expression vector or plasmid containing a recombinant DNA sequence as outlined above. Such vector or plasmid is in accordance with the invention capable of replicating in a Gram positive bacterial host.

Furthermore, the invention covers Gram positive bacterial cells harbouring a recombinant DNA sequence as defined above or transformed by a vector or plasmid containing such recombinant DNA sequence.

Finally, the invention provides a process for selective isolation or identification of Gram positive bacterial cells from a heterologous population of such cells, wherein the cells carry different recombinant surface receptor structures, although each individual cell carries multiple copies of a specific recombinant surface receptor structure. Such process involves the step of allowing said heterologous population of cells to interact with a specific interacting partner, such as an antigen, enabling identification and/or isolation of cells carrying one specific recombinant surface receptor structure. According to one aspect of such inventive process said receptor structures may be constituted by antibodies or active fragments thereof.

It is preferred that said interacting partner is used in an immobilized form, whereby cells carrying a specific structure can be efficiently isolated. Such immobilization is preferably performed onto a solid support, such as in the form of a column.

The present invention will be further illustrated more in detail in the following description of specific embodiments presented in the form of examples. These examples refer to the appended FIGS. 1 to 9, the contents of which will be clear from the legends to FIGS. below.

Starting Materials

Bacterial Strains and Cloning Vectors

*Escherichia coli* strain RR1ΔM15 (Rüther, U., Nucl. Acids Res. 10, 5765–5772 (1982)) was used for the *E. coli* expression and the plasmid constructions. *Staphylococcus xylosus* KL117 (Schleifer and Kloos, Int. J. Syst. Bacteriol. 25, 50–61 (1975)) was used for the expression of recombinant-proteins on the cell surface. pRIT28 (Hultman et al, Nucleos. and Nucleot. 7, 629–637 (1988)) pUC19 (Yanisch-Perron C., Vieira J. and Messing J., Gene 33, 103–119 (2985)) pRIT24 (Hammarberg et al, Proc. Natl. Acad. Sci. 86, 4367–4371 (1989)) pHERAT and pLERAT (A kind gift from Dr. Greg Winter MRC, Cambridge, United Kingdom).

All strains, vectors, oligonucleotides and antibodies used in the examples are available at the Department of Biochemistry and Biotechnology at the Royal Institute of Technology, Stockholm, Sweden.

The vectors pSBB-M3-XM and pSBB-ScFv(D1.3)-XM have been deposited on May 10, 1991, at the Deutsche Sammlung von Microorganismen und Zellkulturen GmbH in Braunschweig, Germany and given the accession numbers DSM 6516 and DSM 6517 respectively, in accordance with the Budapest treaty.

Broth

Tryptic Soy Broth (30 g/l) with Yeast Extract (5 g/l) was from Difco Inc. and dissolved in sterile water and autoclaved before the appropriate antibiotic was added.

Buffers

TST:Tris/HCl 25 mM pH7.4, 150 mM NaCl, 0.05% Tween 20. PBS:0.05M sodium phosphate pH 7.1, 0.15M NaCl.

PCR amplification

PCR amplifications were performed on a Techne Programmable Dri Block PHC-1

10× PCR buffer: 100 mM TRIS/HC1, pH 8.3, 500 mM KC1, 20 mM $Mg^{2+}$, 1% Tween 20, 2 mM dNTP's and oligo nucleotide primers as described in the examples [5 pmole of each]

DNA polymerase: 0.5 units of Ampli Taq® [Perkin Elmer Corp.]

PCR programme: 97° C., 0.5 minutes; 65° C., 1.0 minutes;

72° C., 1.0 minutes.

Oligonucleotides [SEQ ID NOS.:1–8].
KS1: 5'-CCGAATTCGCAGGTCCAACTGAAGGAGTC-3'

KS2: 5'-CGAAGCTTTTAGGATCCTGAGGAGACTGTGAGAGTGG-3'

KS3: 5'-GCGAATTCGGACATCCAGATGACTCAGTC-3'

KS4: 5'-CGAAGCTTTTAGGATCCTTTGATTTCCAGCTTGGTGCC-3'

KS5: 5'-TGGACCCACCACCGCCCGAGCCACCGCCACCTTTGATTTCCAG
     CTTGGTGCC-3'

KS6: 5'-GGGCGGTGGTGGGTCCATGGGCGGCGGATCTCAGGTCCAACTG
     AAGGAGTC-3'

STST 33: 5'-TTGGATCCTGCAGCAATTT-3'

STST 34: 5'-CCGAATTCAAGCTTCGCTCAAGCACCAAAAGAGGAAGAC
         AATAAC-3'

DNA Sequencing

Solid phase DNA sequencing was performed in accordance to Hultman et al [Nucl. Acids. Res. 17, 4937–4946, (1989)].

Affinity Purification of Proteins [HSA and HEL]

Cells harbouring the different constructs were grown over night in broth supplemented with Ampicillin 100 mg/l. The medium was clarified by centrifugation at 5000 g first and then by a second centrifugation at 9000 g. Clarified medium was loaded directly on HSA-Sepharose or HEL-Sepharose. After washing with 1×TST followed by 0.5 mM NH₄Ac, pH 5.0 proteins were eluted with 0.5M HAc, pH 2.8. The absorbtion at 280 nm was measured and relevant fractions were lyophilized.

SDS PAGE

Proteins were dissolved and boiled for 5 min in 2.5% Sodium dodecyl sulphate [SDS], 5% dithiothreitol [DTT] and 0.01% Bromophenol Blue [BFB] before loaded onto a 10–15% gradient polyacrylamide gel for 30 min at 10 mA in accordance with the PHAST™system [Pharmacia-LKB Biotechnology, Sweden]. The gels were subsequently stained with Coomassie Brilliant Blue.

Routine Methods

Methods used routinely in molecular biology are not described, such as restriction of DNA with endonucleases, ligation of DNA fragments etc.

Preparation and Transformation of Protoplasts

The preparations and transformations of protoplasts from *S. xylosus* were performed as described by Götz et al (J. Bacteriol. 145, 74–81 (1981)).

DNA Preparations from Staphylococci

Minipreparations of plasmid DNA from transformed staphylococci were performed using a modified alkaline extraction procedure (Birnboim and Doly, Nucl. Acids Res. 7, 1513–1523 (1979)). Cells harbouring the different constructs were grown over night in 1.5 ml broth supplemented with Chloramphenicol 20 mg/l. Prior the standard protocol, the cells were incubated for one hour at 37° C. with 5 μg lysostaphine in 100 μl saline buffer.

Rabbit Antisera

The rabbit antiserum R120 was obtained from a rabbit immunized two times intramuscularly with 60 μg of preformed influenza membrane glycoprotein ISCOMs (Morein et al., Nature 308, 457–460 (1984)) covalently conjugated with a mixture of the fusion proteins ZZ-M3 and ZZ-M 5 (Ståhl et al., Gene 89, 187–190 (1990)).

The preparation of the influenza ISCOMs and the coupling of the fusion proteins were performed as described by Lövgren et al. (J. Immunol. Meth. 98, 137–143 (1987)). The antiserum R120 reacted strongly with M3 peptide in ELISA and was non-reactive with the BB region and could consequently be used for the detection of M3 peptide on the surface of staphylococci. The antiserum R102 was obtained from a rabbit immunized two times with the fusion protein BB-M5 (Ståhl et al., Gene 89, 187–190 (1990)) in Freund's Adjuvant. Freund's Complete Adjuvant was used for the first injection and Freund's Incomplete Adjuvant was used for the second injection. The antiserum R102 reacted strongly with the BB region in ELISA while no reactivity to the M3 peptide could be demonstrated. The antiserum R102 was therefore suitable for the detection of BB on the surface of staphylococci.

Immunoassay for the Detection of Peptides on the Surface of S. xylosus

Cells harbouring the different constructs were grown at 37° C. over night in broth supplemented with Chloramphenicol (20 mg/l). The cells were washed two times in PBS. 15-well multitest slides (Flow laboratories) were incubated with coating buffer (15 mM $Na_2Co_3$, 35 mM $NaHCO_3$, pH 9.6) in a humid chamber for 30 minutes at room temperature. The coating buffer was displaced by one drop of bacteria ($10^7$ bact./ml) in PBS and the slides were incubated in a humid chamber for 30 minutes at room temperature. Unbound bacteria were washed away with PBS and the monolayer of cells was fixed for a few seconds with 1% glutaraldehyde in PBS. Finally the slides were washed in destined water and air dried before storage at −20° C. The rabbit antisera were diluted 1:1000 in PBS, one drop added to each well, and incubated in a humid chamber for 30 minutes at room temperature. After washing 4 times with PBS, the slides were incubated with biotinylated anti-rabbit IgG-molecules (15 μg/ml) (Vector, USA) for 30 minutes and washed once again in PBS before the addition of avidine-conjugated fluorescein isothiocyanate (FITC)(50μg/ml) (Vector, USA) for 30 minutes incubation. Finally, the slides were washed, ethidium bromide was added to visualize bacterial DNA, and examined under a UV-microscope.

Legend to Figures

FIG. 1A A schematic drawing of the gene encoding staphylococcal protein A with its different regions. S is the signal sequence. E, D, A, B and C encode the highly homologous IgG-binding domains. X encodes the cell wall spanning region and M the mebrane anchoring region.

FIG. 1B An illustration of processed protein A bound to the outer cell surface of staphylococci.

FIG. 2A The plasmids pSBBmp18XM and pSBBm3XM described in Example 1. Note that the BB-region in this case is the serum albumin binding region based on streptococcal protein G. Abbreviations: bla, β-lactamase encoding gene; cat, chloramphenicol acetyl transferase encoding gene; OriE, origin of replication from E. coli; OriS, origin of replication from S. aureus.

FIG. 2B An illustration of the processed and secreted expression products, encoded from plasmids pSBBmp18XM and pSBBM3XM, bound to the cell surface of staphylococci.

FIG. 3 Immunofluorescence of immobilized S. xylosus cells expressing BB on the cell surface. The reactivity is obtained with BB-specific antisera (R120). Note that the internal part of the cells is enlightened by the ethidium bromide staining.

Figure 4:
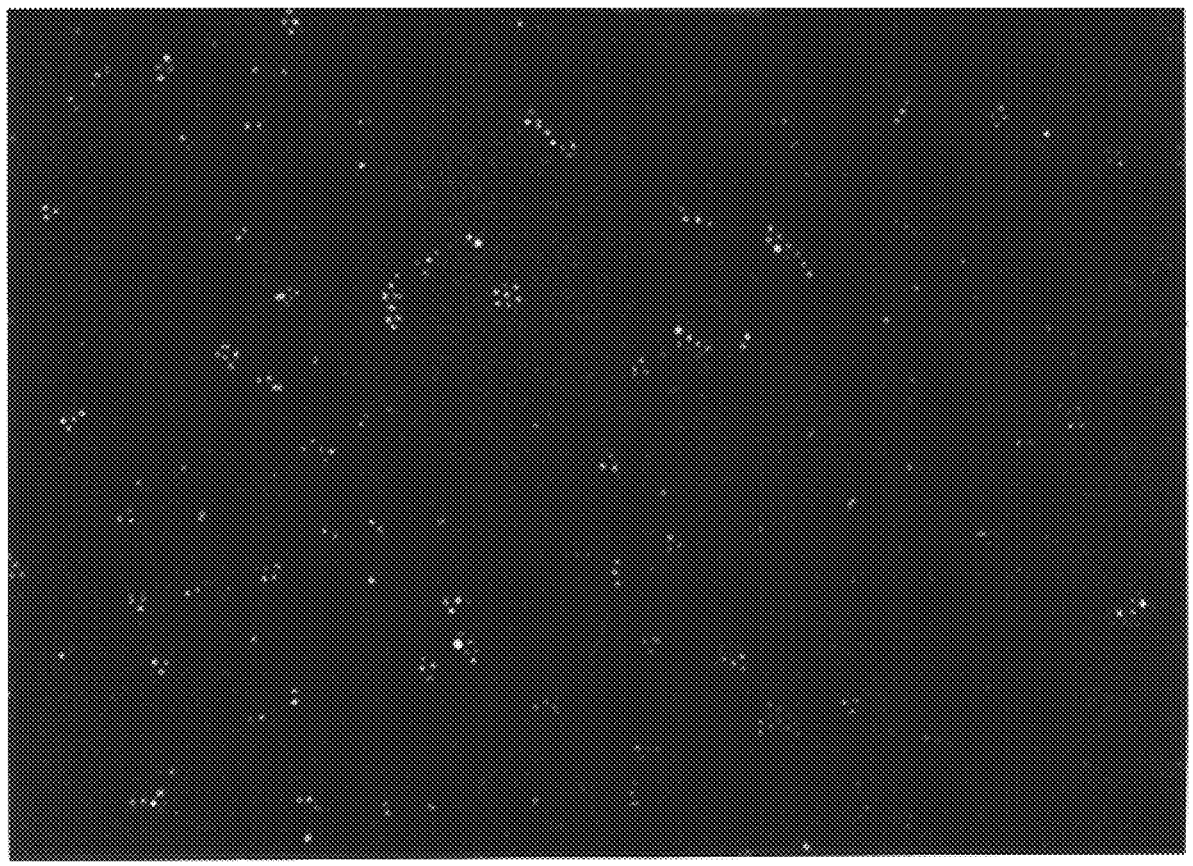

FIG. 4 Immunofluorescence of immobilized S. xylosus cells expressing BBM3 on the cell surface. The reactivity is obtained with M3-specific antisera (R102). Note that the internal part of the cells is enlightened by the ethidium bromide staining.

Figure 5:
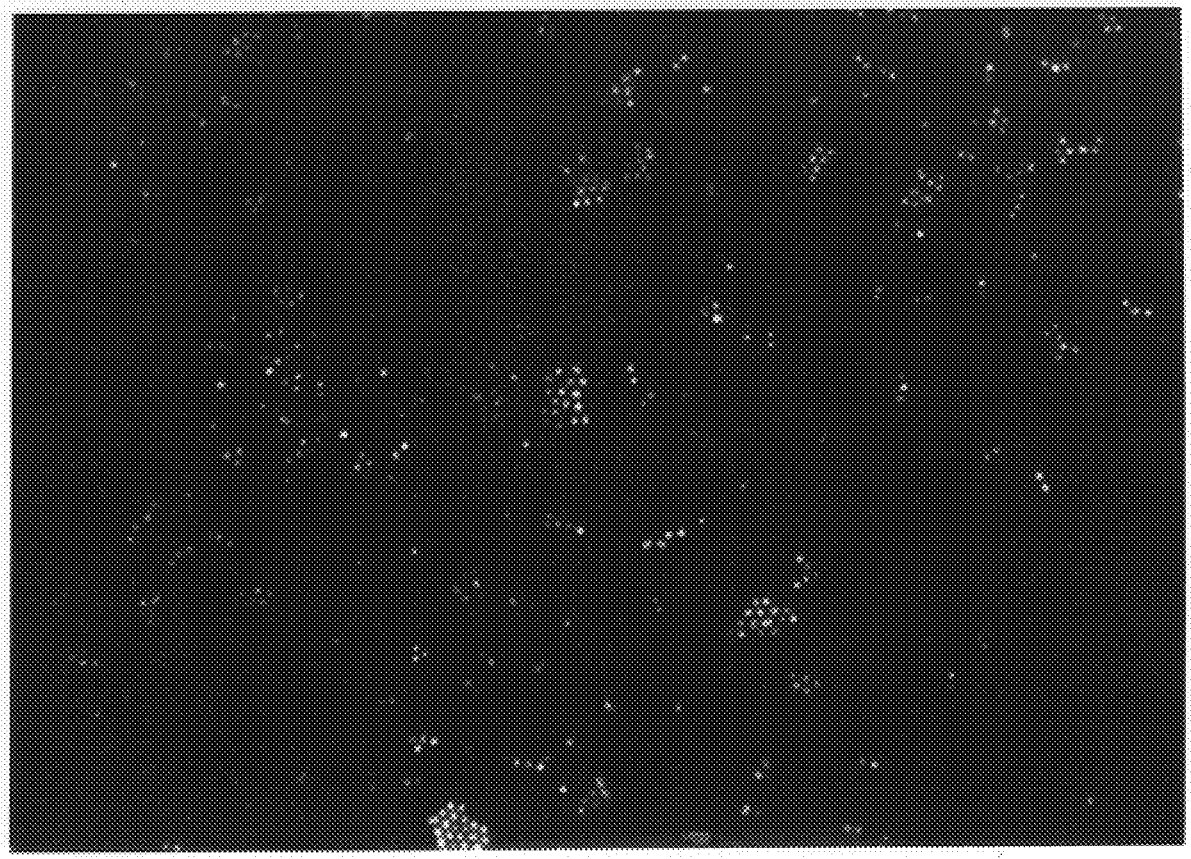

FIG. 5 Immunofluorescence of immobilized S. xylosus cells expressing BBM3 on the cell surface. No reactivity could be obtained using preimmune sera. Note that the internal part of the cells is enlightened by the ethidium bromide staining.

Figure 6:
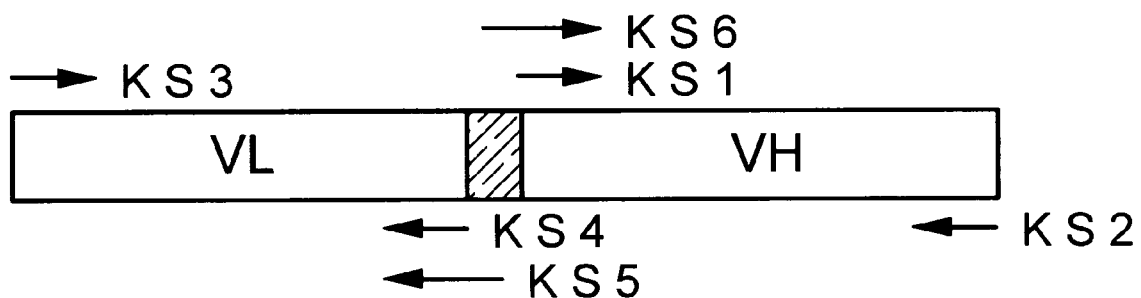

FIG. 6 Schematic representation of the gene encoding the scFv fragment of the mouse antilysozyme antibody D1.3. The annealing sites for the different oligonucleotides are indicated by the arrows.

FIG. 7 [SEQ ID NO.:11] Schematic description of the pSBB-scFv-XM plasmid encoding the BB-scFv-XM fusion protein. Some relevant restriction enzyme recognition sites are shown. CAT: chloramphenicol acetyl transferase.

Figure 8:
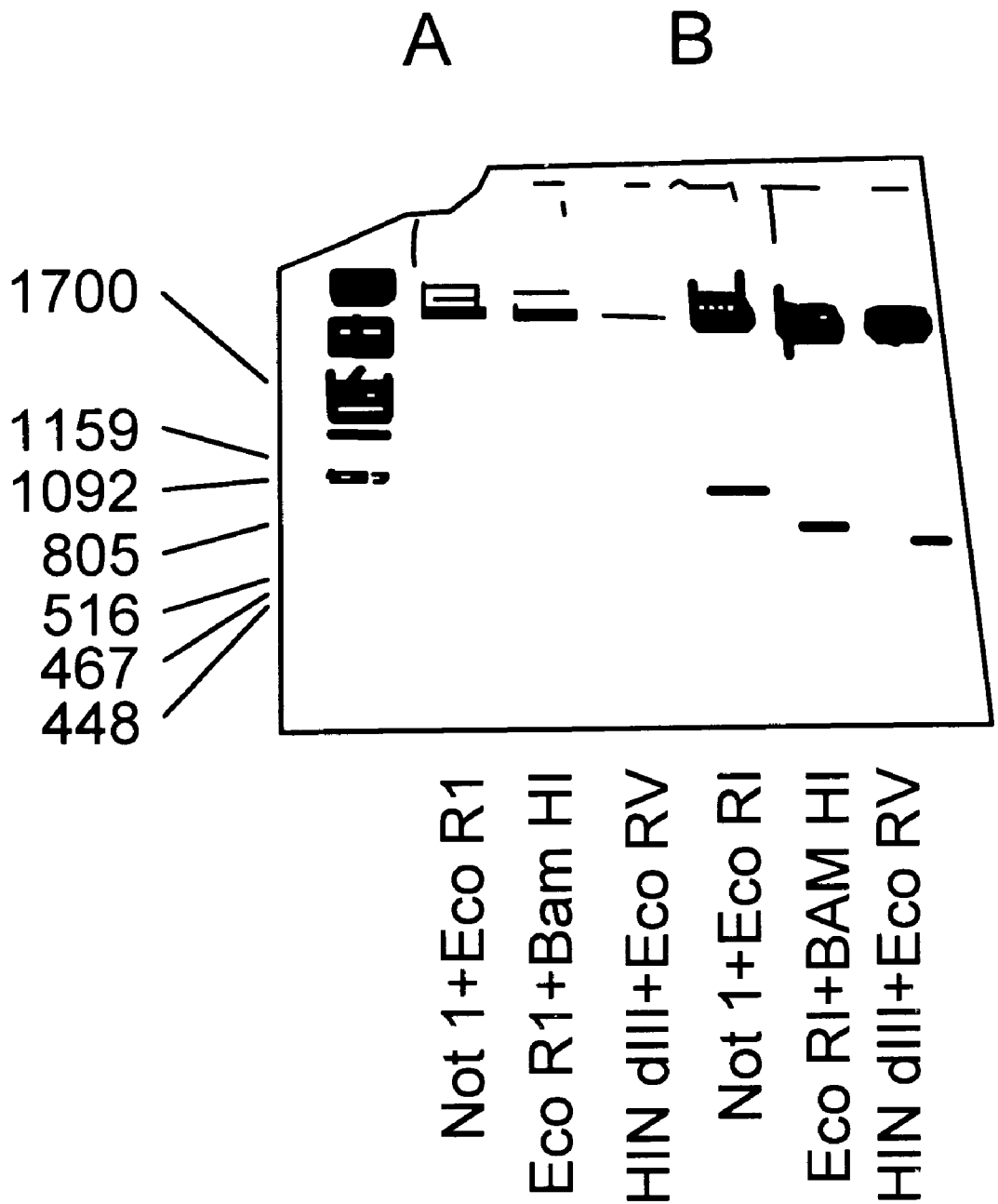

FIG. 8 Polaroid image of an ethidium bromide stained and UV [254 nm] exposed gel, containing the different DNA fragments of the pSBB-scFv-XM plasmid obtained after digestion with the indicated restriction enzymes. Panel A: Plasmid prepared from S. xylosus cells; panel B: plasmid prepared from E. coli cells. Marker DNA fragment sizes are indicated [left].

Figure 9:
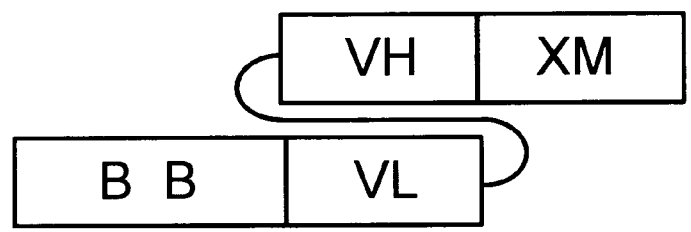

FIG. 9 Schematic representation of the expected orientation in the S. xylosus host cell wall of the BB-scFv-XM fusion protein encoded by the pSBB-scFv-XM plasmid.

Figure 10:
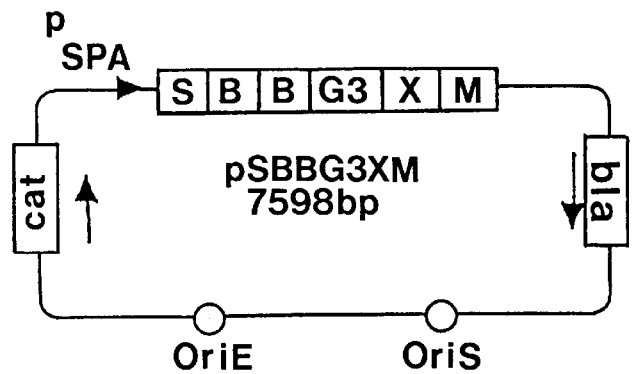

FIG. 10 Schematic description of the pSBBG3XM plasmid harbored by the S. xylosus cells used for the oral administration of the mice. S, signal peptide derived from staphylococcal protein A[SPA]; BB, serum albumin binding region derived from streptococcal protein G; G3, the three-copy RSV epitope; XM, the cell wall anchoring region from SPA; bla, beta-lactamase; OriE, origin of replication for E. coli; OriS, origin of replication for S. xylosus; cat, chlcramphenicol acetyl transferase; Pspa, promoter from the spa operon.

Figure 11:
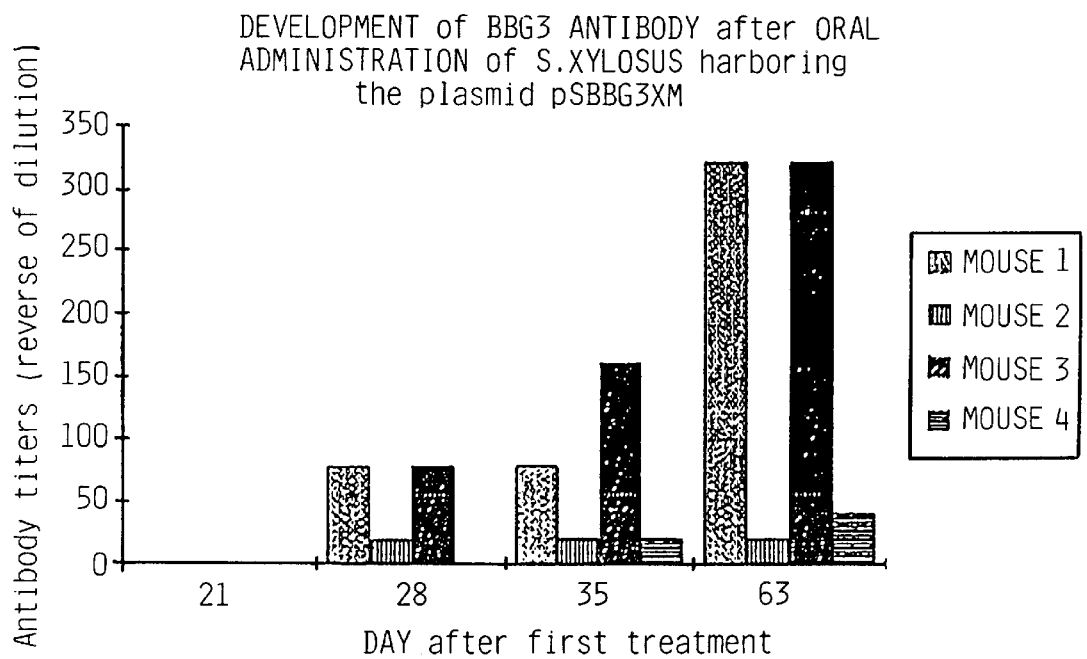

FIG. 11 Bardiagram representation of the results from the ELISA assay for the detection of anti-BBG3 antibodies present in the blood of the immunized mice at different time points after the first oral distribution.

EXAMPLE I

By NotI-NdeI digestion of the E. coli-staphylococci shuttle vector pRIT16 (Abrahmsén et al., Nucl. Acids Res. 14, 7487–7500 (1986)), the gene for staphylococcal protein A (SPA) was replaced for a NotI-NdeI gene fragment restricted from plasmid pEZZ318T (Nygren et al., J. Molec. Recogn. 1, 69–74 (1988)) encoding a synthetic divalent IgG-binding domain, ZZ, preceded by the transcription, translation and secretion signals of SPA. The resulting plasmid pSZZmp18T contained the origins of replication for both E. coli and Staphylococcus aureus. A gene fragment encoding the IgG-binding regions A, B and C plus the cellwall spanning region X and membrane anchoring region M (FIG. 1) of SPA, was restricted from plasmid pSpA8 (Uhlén et al., J. Biol. chem. 259, 1695–1702 (1984)) using HindIII and EcoRV, and inserted downstream of the mp18 multicloning site (Yanisch-Perron et al., Gene 33, 103–119

(1985)) in plasmid pSZZmp18T, previously restricted with the same enzymes. The resulting vector was denoted pSZZmp18ABCXM. This plasmid was digested with HindIII and PstI thus deleting a gene fragment encoding regions A, B, C and X and half of region M of SPA. The complete sequence of region X and M could be restored applying a polymerase chain reaction (PCR) strategy. A PCR amplification was performed using STST 34 as the upstream primer, STST33 as the downstream primer and plasmid pSpA8 as DNA template. The upstream primer generated a HindIII recognition site by its non-annealing 5' sequence and the downstream primer overlapped a native PstI recognition sequence in the M region of SPA. The PCR amplified fragment could thus be restricted with HindIII and PstI and subcloned to plasmid pRIT28 (Hultman et al., Nucleos. and Nucleot. 7, 629–638 (1988)), previously restricted with the same enzymes, yielding plasmid pRIT28XM. The nucleotide sequence of the PCR subcloned fragment was verified by solid phase DNA sequencing (Hultman et al., Nucl. Acids Res. 17, 4937–4946 (1989)). By HindIII-PstI restriction of pRIT28XM the gene fragment, encoding region X and half of region M of SPA, could be isolated and fused to the HindIII-PstI digested plasmid pSZZmp18ABCXM (described above) resulting in plasmid pSZZmp18XM, with complete and in frame regions X and M downstream of the mp18 multicloning site. By NotI-EcoRI digestion of plasmid pSZZmp18XM the ZZ encoding gene fragment could be replaced for a NotI-EcoRI fragment restricted from plasmid pB1B2mp18 (Ståhl et al., J. Immunol. Meth. 124., 43–52 (1989)), encoding a serum albumin binding region of streptococcal protein G, denoted BB, preceded by the transcription, translation and secretion signals of SPA. The resulting vector pSBBmp18XM (FIG. 2A) contained the origins of replication for both E. coli and Staphylococcus aureus. The mp18 multicloning site in the general expression vector pSBBmp18XM was removed by EcoRI-HindIII restriction. A gene fragment, encoding a highly repetitive peptide M3 (Ståhl et al., Gene 89, 187–193 (1990)), was cut out from plasmid pRIT28M3 (Ståhl et al., Gene 89, 187–193 (1990)) where the stop codon ending the M3 sequence first was removed by site directed solid phase in vitro mutagenesis (Hultman et al., Nucl. Acids Res. 18, 5107–5112 (1990)). The M3 encoding, EcoRI-HindIII restricted, gene fragment was ligated to the similarly digested pSBBmp18XM, yielding plasmid pSBBM3XM (FIG. 2A). The M3 polypeptide is derived from the highly immunogenic C-terminal part of the malaria blood-stage antigen Pf155/RESA (Berzins et al., Proc. Natl. Acad. Sci. USA 83, 1065–1069 (1986)).

Plasmid pSBBmp18XM encode a tripartite fusion protein, comprising the signal peptide from SPA, the serum binding BB part derived from streptococcal protein G and the cellwall binding XM regions from SPA. Upon secretion through the cell membrane, the signal peptide is cut off. Plasmid pSBBM3XM encode a tetrapartite fusion protein where the malarial antigenic peptide M3 is placed between the BB and XM regions (FIG. 2B).

Plasmids pSBBmp18XM and pSBBM3XM are trasformed to protoplasts prepared from Staphylococcal xylosus (see under "Starting materials" for details). As shown in Table 1, an immunoassay using polyclonal rabbit antisera specific for BB or M3, respectively, revealed that S. xylosus cells harbouring plasmid pSBBmp18XM expressed BB on the cell surface (FIG. 3) whereas pSBBM3XM containing cells expressed both BB and M3 on the cell surface (FIG. 4), indicating that both the secretion signals and the cell wall binding moiety, XM, are functional when expressing recombinant fusion proteins by this manner. S. xylosus cells without plasmid were negative for both BB and M3 specific antisera, respectively, and preimmune sera were negative in all cases (FIG. 5).

TABLE 1

| | Rabbit antisera | | |
|---|---|---|---|
| S. xylosus cells harbouring | Preimmune | BB-specific (R120) | M3-specific (R102) |
| pSBBmp18XM | − | + | − |
| pSBBM3XM | − | + | + |
| No plasmid | − | − | − |

EXAMPLE II

By PCR amplification using the oligonucleotides primer pairs KS1/2 and KS3/4 respectively, on the plasmid templates pHERAT and pLERAT harbouring the variable domains of the heavy [pHERAT] and light [pLERAT] chains of the anti-lysozyme antibody D1.3 [McCafferty et al 1990, Nature 348, 552–554], the gene fragments encoding the two variable domains could be isolated. By the use of the primer-incorporated suitable restriction enzyme recognition sites Eco RI and Bam HI, the fragments were inserted into pRIT28, adapted for solid phase sequencing.

After confirmation of the correct sequences, the resulting plasmids pRIT28-VH and pRIT28-VL were separately used as templates in a subsequent PCR amplification using oligonucleotide primer pairs KS6/2 [pRIT28-VH] and KS3/5 [pRIT28-VL], respectively. Approximately five [5] nanograms each of the resulting PCR products were subsequently mixed, heated to 85° C. and thereafter let to cool to room temperature. After addition of 0.5 units of Taq polymerase [Perkin Elmer corp.], PCR buffer, two standard cycles of PCR were run in order to obtain double stranded DNA. This procedure results in the linking of the two immunoglobulin encoding gene fragments due to the overlapping sequences incorporated during the second PCR by the KS5 and KS6 oligonucleotides. The linking DNA sequence encodes a highly flexible, 15 amino acid residues bridging peptide between the two immunoglobulin domains. The resulting 730 basepair gene fragment thus encodes a single chain Fv [scFv] fragment of the anti-lysozyme antibody D1.3 [FIG. 6] as described by the schematic representation:

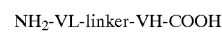

NH$_2$-VL-linker-VH-COOH in order to obtain sufficient amounts for further cloning of the scFv encoding fragment, 20 additional PCR cycles were executed employing the outer primers KS3 and KS2. The resulting PCR product was restricted with restriction enzymes Eco RI and Bam HI and subsequently ligated into the cloning vector pUC19. After confirmation of the sequence, a clone containing the correctly assembled scFv gene fragment was Eco RI and Bam HI restricted and the 730 basepair fragment was inserted into the Eco RI and Bam HI sites of the E. coli expression vector pRIT24 [Hammerberg et al Proc. Natl. Acad. Sciences, USA, 86, 4367–4371]. The resulting construct pRIT24-scFv thus encodes the tripartite fusion ZZ-scFv-BB. E. coli cells transformed with the pRIT24-scFv were grown over night at 30° C. in Tryptic Soy Broth+Yeast Extract supplemented with ampicillin [100mg/l].

In order to investigate the stability and biological activity of the recombinant ZZ-scFv-BB fusion protein, culture medium from the over night fermentation was passed through Human Serum Albumin [HSA] and Hen Egg-White Lysozyme [HEL] Sepharose columns respectively. Proteins eluted from the columns by 0.5M HAc/NH$_4$Ac pH2.8 were lyophilized and analyzed by SDS-PAGE. The major band for both the HSA- and HEL-affinity purified material was found to be of full-length. The successful affinity purification of the ZZ-scFv-BB fusion protein using HEL suggests that the scFv immunoglobulin fragment is able to fold into a native, biologically active-structure although flanked by the two affinity tails ZZ and BB.

Described in Example 1 is the construction of the shuttle vector pSBBmp18XM, able to replicate both in E. coli and Staphylococcus cells. In order to adapt this vector for the insertion of the scFv fragment, the mp18 linker was substituted with the shorter mp8 linker derived from M13mp8 [Messing et al, 1982, Gene 19, 269–276] to yield pSBBmp8XM. The scFv encoding gene fragment was released from the pUC19-scFv plasmid by Eco RI and Bam HI restriction and subsequently ligated into the pSBBmp8XM vector.

S. xylosus cells were transformed with the resulting pSBB-scFv-XM construct [FIG. 7] and viable colonies were grown over night at 37° C. in TSB supplemented with chloramphenicol [20 mg/l] for plasmid preparation. Restriction enzyme mapping of the pSBB-scFv-XM construct, prepared from the transformed staphylococci cells, was in agreement with the expected result [FIG. 8]. This shows that the pSBB-scFv-XM construct is genetically stable within the Staphylococcus host.

This construct encodes the BB-scFv-XM fusion protein designed to be incorporated into the host cellwall [FIG. 9].

EXAMPLE III

Development of specific antibodies in mice after oral administration.

A gene encoding a peptide, G3, containing three [3] copies of the Respiratory syncytial virus [RSV] glycoprotein G epitope [Trudel et al (1991), Virology 185: 749–757] C-terminal repeat sequences, VSICSNNPTCWAISKN, was constructed using the oligonucleotides: TH5 [SEQ ID NO.:9 ]:5'-ATGTATCTA TCT-GCTCTAACAACCCGACTTGTTGGGCTATCTCCA AAA-3' and TH6 [SEQ ID NO.:10]: 5'-ACATTTTTG GAGATAGCCCAACAAGTCGGGTTGTTAGAGCAG ATAGAT-3' according to the polymerization concept described for the construction of the M3 peptide described in Example I and inserted into pRIT28E yielding pRIT28EG3. The nucleotide sequence of the G3 encoding gene was verified by solid phase DNA sequencing [Hultman et al (1989) Nucl. Acids Res. 17: 4937–4946]. The G3 gene fragment was cut out from pRIT28EG3 with EcoRI and HindIII and ligated to the similarly digested pBB2mp18 vector [Ståhl et al (1989), J. Imm. Meth. 124: 43–52]. The resulting vector, pBBG3 [5153 bp], encodes a fusion protein designated BBG3 [30.9 kDa], consisting of the serum albumin binding region from streptococcal protein G [SPG] and the tripeptide repeat. E. coli cells harboring the pBBG3 . plasmid were grown over night at 37° C. in 500 ml tryptic soy broth [30 g/l] supplemented with ampicillin [100 mg/l]. The fusion proteins were purified from the medium and the pariplasmic space by affinity chromatography on HSA-Sepharose according to Nygren et al [J. Mol. Recognit. 1:69–74].

The G3 encoding gene fragment was recovered from pRIT28EG3 plasmid restricted with EcoRI and HindIII after the removal of the stop codon ending the G3 sequence by solid phase site directed mutagenesis as described for the M3 gene in Example I. The restricted fragment was ligated to the similarly restricted pSBBmp18XM, yielding plasmid pSBBG3XM [FIG. 10]. Plasmid pSBBG3XM encodes a tetrapeptide fusion protein, comprising the signal peptide from SPA, the serum albumin binding BB region derived from SPG, the RSV antigenic peptide G3 and the cellwall binding XM regions from SPA.

Plasmids pSBBmp18XM and pSBBG3XM were transformed to protoplasts prepared from Staphylococcus xylosus [for details, see "Starting materials"] and the cells grown over night. Four female mice OFI [IFFA CREDO, France] six weeks of age at the beginning of the experiments, were each orally given $10^{10}$ S. xylosus bacteria [counted by microscope using an improved Neubauer counting chamber] from over night cultures harboring the pSBBG3XM plasmid each tuesday, wednesday, thursday and friday during a three week period followed by a second period of three weeks after day 43. Blood was collected individually at days 21, 28, 35 and 63 and tested for the presence of anti-BBG3 antibodies using purified BBG3 protein as coating antigen in an ELISA assay: microtiter plates were coated over night with a 1.25 µg/ml solution of BBG3 , followed by a two hours saturation with 1% skimmed milk in PBS. The blood samples from the immunized mice were subsequently loaded and after incubation and subsequent extensive rinse, the bound antibodies were detected using antimouse IgG-alkaline phosphatase conjugate [Sigma Inc. reagent No. A1902] together with chromogenic alkaline phosphatase substrate allowing monitoring at 405 nm. Tests were done in triplicates with serum taken at day zero to be used as negative control and a rabbit anti-BBG3 polyclonal sera was used as positive control. The results shown in FIG. 11 show the development of BBG3 -specific immune responses in all four animals during the 63 days of treatment.

We claim:

1. A recombinant DNA encoding a fusion polypeptide which upon expression in a Gram positive bacterium is expressed on the surface thereof, which recombinant DNA comprises (i) a first DNA fragment which encodes for a signal peptide operable in a Gram positive bacterium, which first DNA fragment is operably linked to ii a second DNA fragment encoding for a second polypeptide other than the IgG binding domain of Staphylococcus protein A wherein said second DNA fragment is operably linked to (iii) a third DNA fragment which includes only the coding regions of either Staphylococcus protein A or a Streptococcal protein G that are responsible for cell wall spanning and membrane anchoring.

2. The recombinant DNA of claim 1 wherein said second DNA fragment encodes an immunogenic polypeptide capable of specifically binding to an antibody.

3. The recombinant DNA of claim 2 wherein said immunogenic polypeptide is capable of specifically binding to or inducing the formation of antibodies.

4. The recombinant DNA of claim 2 wherein said immunogenic polypeptide is capable of inducing a specific antibody response in a host.

5. The recombinant DNA of claim 1 wherein said second DNA fragment encodes an antigenic polypeptide or a single chain antibody (scFv).

6. The recombinant DNA of claim 1 wherein said third DNA fragment encodes for the cell wall spanning and membrane anchoring region of Streptococcal protein G.

7. An expression vector which contains a recombinant DNA according to claim 6 which is capable of replicating in a Gram positive bacterium.

8. The expression vector of claim 7 wherein said vector is a plasmid.

9. A Gram positive bacterium which has been transformed with a vector which comprises a recombinant DNA according to claim 6 and which expresses on its surface a fusion protein comprising said second polypeptide wherein said second polypeptide is one not normally expressed on the surface of said Gram positive bacterium.

10. The recombinant DNA of claim 1 wherein said third DNA fragment encodes for the cell wall spanning and membrane anchoring region of Staphylococcal protein A.

11. The recombinant DNA of claim 10 wherein said first DNA fragment encodes the signal peptide of Staphylococcal protein A.

12. An expression vector which contains a recombinant DNA according to claim 11 which is capable of replicating in a Gram positive bacterium.

13. The expression vector of claim 12 which is a plasmid.

14. A Gram positive bacterium which has been transformed by a vector which comprises a recombinant DNA according to claim 11 and which expresses on its surface a fusion protein comprising said second polypeptide wherein said second polypeptide is one not normally expressed on the surface of said Gram positive bacterium.

15. An expression vector which contains a recombinant DNA according to claim 10 which is capable of replicating in a Gram positive bacterium.

16. The expression vector of claim 15 wherein said vector is a plasmid.

17. A Gram positive bacterium which has been transformed by a vector which comprises a recombinant DNA according to claim 10 and which expresses on its surface a fusion protein comprising said second polypeptide wherein said second polypeptide is one not normally expressed on the surface of said Gram positive bacterium.

18. The recombinant DNA of claim 11 wherein said first DNA fragment encodes a signal peptide which is expressed by a Gram positive bacterial cell.

19. An expression vector which contains a recombinant DNA according to claim 1 which is capable of replicating in a Gram positive bacterium.

20. The expression vector of claim 19 wherein said vector is a plasmid.

21. A Gram positive bacterium which has been transformed with a vector which comprises a recombinant DNA according to claim 1 and which expresses on its surface a fusion polypeptide which comprises said second polypeptide wherein said second polypeptide is one not normally expressed on the surface of said Gram positive bacterium.

22. A method for identifying from a population of Gram positive bacterial cells those cells which express on their surface a polypeptide which specifically binds to a putative binding partner comprising:

obtaining a population of Gram positive bacterial cells which contain and express on their surface a recombinant fusion protein encoded by a recombinant DNA according to claim 1;

contacting said population of cells which express on their surface a fusion polypeptide encoded by said recombinant DNA with a putative binding partner under conditions which permit the putative binding partner to bind to the second polypeptide; and selecting Gram positive cells which specifically bind the putative binding partner and therefore express on their surface a polypeptide which specifically binds the putative binding partner.

23. The method of claim 22 wherein the second DNA fragment comprised in said recombinant DNA encodes for a receptor.

24. The method of claim 22 wherein the second DNA fragment comprised in said recombinant DNA encodes for a single chain antibody or an antigenic polypeptide.

25. The method of claim 24 wherein the third DNA comprised in said recombinant DNA include the cell wall spanning and membrane anchoring regions Staphylococcal protein A.

26. The method of claim 25 wherein the signal peptide encoded by the first DNA contained in said recombinant DNA is the signal peptide of Staphylococcal protein A.

27. The method of claim 26, wherein the Gram positive bacterial cells are Staphylococcal bacterial cells.

28. The method of claim 27, wherein said Gram positive bacterial cells are *Staphylococcus xylosus* cells.

29. The method of claim 26 wherein said Gram positive bacterial cells which express on their surface a polypeptide which specifically binds the putative binding partner are Staphylococcus cells.

30. The method of claim 29 wherein said Staphylococcus cells are *Staphylococcus xylosus*.

31. The method of claim 22 wherein the putative binding partner is in an immobilized form.

32. The method of claim 31 wherein the putative binding partner is immobilized to a solid support.

33. A method for expressing a fusion polypeptide on the surface of a Gram positive bacterial cell, which method comprises transforming a Gram positive bacterial cell with a recombinant DNA encoding said fusion polypeptide which is encoded by a recombinant DNA according to claim 2, and culturing said transformed Gram positive bacterial cell under conditions that result in the expression of said fusion polypeptide on the surface of said Gram positive bacterial cell.

34. The method of claim 33, wherein said fusion polypeptide comprises an immunogenic polypeptide capable of specifically binding to an antigen.

35. The method of claim 33, wherein said fusion polypeptide comprises an immunogenic polypeptide capable of specifically binding to or inducing the formation of antibodies.

36. The method of claim 33, wherein said fusion polypeptide comprises an immunogenic polypeptide capable of specifically inducing a specific antibody response in a host.

37. The method of claim 33, wherein said fusion polypeptide comprises an immunogenic polypeptide which is an antigenic polypeptide or a single chain antibody (scFv).

38. The method of claim 33, wherein said fusion polypeptide comprises the cell spanning and membrane-anchoring regions of Streptococcal protein G.

39. The method of claim 33, wherein the cell wall spanning and membrane-anchoring region is that of Staphylococcal protein A.

40. The method of claim 33, wherein said recombinant DNA comprises a DNA encoding the signal peptide of Staphylococcal protein A.

41. The method of claim 33, wherein said recombinant DNA comprises a DNA encoding a signal peptide which is expressed by a Gram positive bacterial cell.

* * * * *

UNITED STATES PATENT AND TRADEMARK OFFICE
CERTIFICATE OF CORRECTION

PATENT NO. : 5,958,736
DATED : September 28, 1999
INVENTOR(S) : Stefan Ståhl et al.

It is certified that error appears in the above-identified patent and that said Letters Patent is hereby corrected as shown below:

On the cover page, the following should read as:
[63] Related U.S. Application Data Continuation of application No. 08/140,138, filed as application No. PCT/SE92/00304, May 11, 1992.

Column 1:
Line 7 and 8, should read as follows:
--This application is a continuation of application Ser. No. 08/140,138, filed as PCT/SE92/00304, May 11, 1992.

Signed and Sealed this

Twelfth Day of June, 2001

Attest:

NICHOLAS P. GODICI
Attesting Officer  Acting Director of the United States Patent and Trademark Office